(12) United States Patent
Newman et al.

(10) Patent No.: US 11,518,562 B2
(45) Date of Patent: Dec. 6, 2022

(54) STERILE PACKAGING OF FLUENT MATERIALS

(71) Applicant: STERAFILL LIMITED, Carmarthen (GB)

(72) Inventors: Paul Newman, Carmarthen (GB); Mark Blackman, Branshott (GB)

( * ) Notice: Subject to any disclaimer, the term of this patent is extended or adjusted under 35 U.S.C. 154(b) by 0 days.

(21) Appl. No.: 16/310,929

(22) PCT Filed: Jun. 21, 2017

(86) PCT No.: PCT/EP2017/065302
§ 371 (c)(1),
(2) Date: Dec. 18, 2018

(87) PCT Pub. No.: WO2017/220688
PCT Pub. Date: Dec. 28, 2017

(65) Prior Publication Data
US 2019/0217983 A1 Jul. 18, 2019

(30) Foreign Application Priority Data

Jun. 21, 2016 (GB) ..................... 1610853

(51) Int. Cl.
*B65B 55/10* (2006.01)
*B65B 3/02* (2006.01)
(Continued)

(52) U.S. Cl.
CPC .............. *B65B 55/103* (2013.01); *A61L 2/14* (2013.01); *A61L 2/26* (2013.01); *B65B 3/02* (2013.01);
(Continued)

(58) Field of Classification Search
CPC ......... B65B 55/103; B65B 3/02; B65B 55/08; B65B 55/04; B65B 55/00; B65B 55/10
(Continued)

(56) References Cited

U.S. PATENT DOCUMENTS 3,347,012 A 10/1967 Scholle
3,850,207 A * 11/1974 Loliger ................. B65B 55/103
141/90
(Continued)

FOREIGN PATENT DOCUMENTS

EP 0271760 A2 6/1988

OTHER PUBLICATIONS

International Search Report in corresponding PCT application No. PCT/EP2017/065302, dated Sep. 27, 2017, pp. 5.
(Continued)

*Primary Examiner* — Robert F Long
*Assistant Examiner* — Xavier A Madison
(74) *Attorney, Agent, or Firm* — Tredecim LLC; Sean L. Sweeney

(57) ABSTRACT

Described herein is a method of forming individual tubes or sachets containing fluent material, and a packaging machine for doing so, are described. The side of the foil which will be in contact with the fluent material when the package is formed is exposed to plasma in mist or aerosol form as the tube or sachet is formed from a strip of laminate material (1), which is folded about a former (2) into a closed tube or sachet which passes over the open end of a dispensing tube (3) from which the fluent material is dispensed. A mist of plasma is injected into the interior of the material tube as it is formed, extracted from the area once it has passed over the interior walls of the laminate tube.

4 Claims, 1 Drawing Sheet

(51) Int. Cl.
  *B65B 9/20* (2012.01)
  *A61L 2/14* (2006.01)
  *A61L 2/26* (2006.01)
  *B65B 55/02* (2006.01)
  *B65B 55/08* (2006.01)

(52) U.S. Cl.
  CPC .............. *B65B 9/20* (2013.01); *B65B 55/027* (2013.01); *A61L 2202/15* (2013.01); *A61L 2202/23* (2013.01); *B65B 55/08* (2013.01)

(58) Field of Classification Search
  USPC .......................................................... 53/426
  See application file for complete search history.

(56) References Cited

U.S. PATENT DOCUMENTS

| | | | | |
|---|---|---|---|---|
| 4,537,007 | A * | 8/1985 | Lattanzi | B65B 55/103 |
| | | | | 53/425 |
| 4,597,242 | A | 7/1986 | Hendriks et al. | |
| 4,606,174 | A * | 8/1986 | Berg | B65B 9/2049 |
| | | | | 53/451 |
| 5,569,438 | A * | 10/1996 | Hilmersson | A61L 2/18 |
| | | | | 53/425 |
| 6,488,889 | B1 * | 12/2002 | Stahlecker | A61L 2/14 |
| | | | | 250/455.11 |
| 7,958,697 | B2 * | 6/2011 | Rapparini | B65B 55/106 |
| | | | | 53/425 |
| 9,371,146 | B2 * | 6/2016 | Tsuruta | B65B 55/103 |
| 2003/0177739 | A1 * | 9/2003 | Lewis, Jr. | B65B 9/20 |
| | | | | 53/425 |
| 2009/0282784 | A1 * | 11/2009 | Ferrarini | B65B 1/02 |
| | | | | 53/167 |
| 2010/0209290 | A1 * | 8/2010 | Cirri | A61L 2/082 |
| | | | | 422/22 |
| 2012/0219455 | A1 * | 8/2012 | Meinzinger | A61L 2/087 |
| | | | | 422/22 |
| 2013/0136655 | A1 * | 5/2013 | Soberon | A61L 2/26 |
| | | | | 422/29 |
| 2014/0322096 | A1 | 10/2014 | Pelfrey et al. | |

OTHER PUBLICATIONS

Written Opinion in corresponding PCT application No. PCT/EP2017/065302, dated Sep. 27, 2017, pp. 3.

* cited by examiner

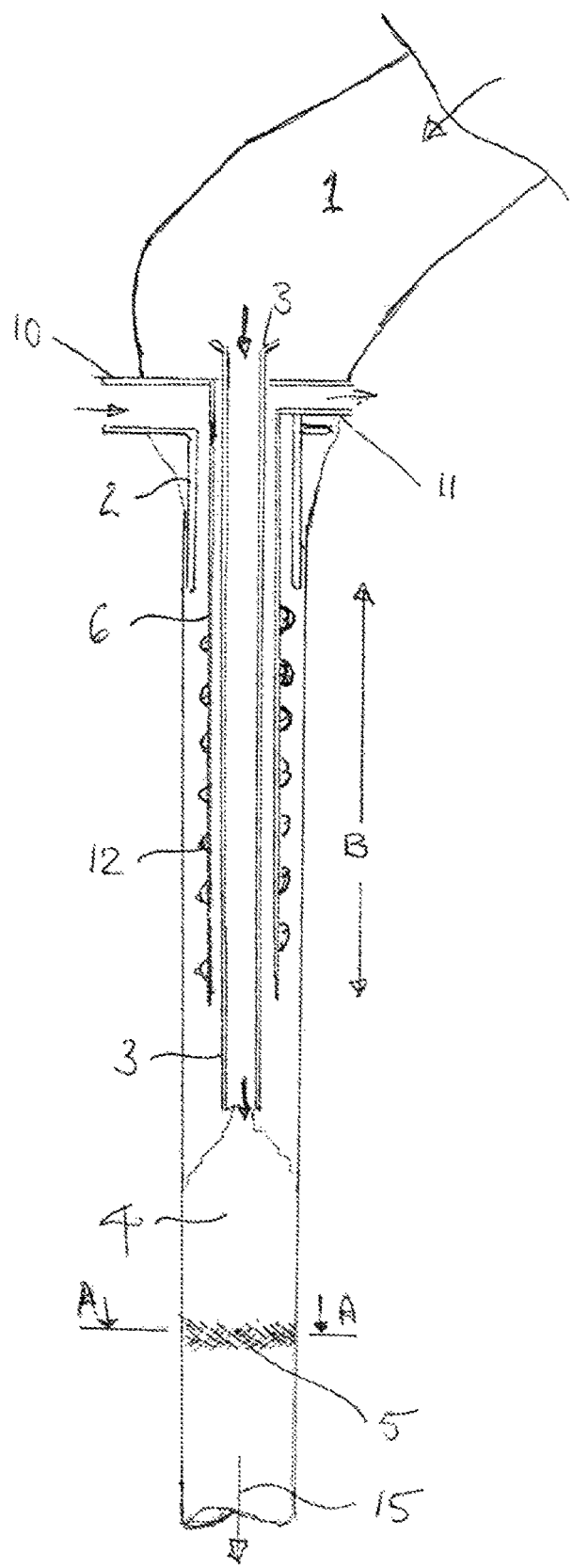

STERILE PACKAGING OF FLUENT MATERIALS

CROSS-REFERENCE TO RELATED APPLICATIONS

This application a national phase application of PCT Application No. PCT/EP2017/065302, filed Jun. 21, 2017, which claims priority to United Kingdom application number 1610853.2, filed Jun. 21, 2016, the entire contents of which are herein incorporated by reference.

BACKGROUND

1. Field of Invention

This invention relates to the sterile packaging of fluent materials.

2. Discussion of Background Information

A well-known form of packaging for fluent materials in individual small quantities is that of a sealed foil tube or sachet. The foil is usually a laminate material. Typical examples of products which may be packaged in this way are dairy products, such as milk or cream, sauces, such as tomato sauce or soy sauce, and granular materials, such as sugar or soluble coffee extract granules. It is clearly desirable for any such product which is to be consumed, and where the product may not be brought into use, i.e. the package may not be opened for some considerable time after it has been manufactured, that the interior is sterile.

In order to achieve this, it is known to sterilise the laminate material from which the tube or sachet is formed by immersing it in an appropriate sterilising medium, for example a 30 to 35% aqueous hydrogen peroxide bath, or by way of electron beam irradiation whereafter the laminate is either slit to form strips of the desired width in a mutilane machine or formed to make the tube, sachet or package which are then fed into automatic filling machinery which forms the strip into a sealed tube, a suitable quantity of material is then fed into the tube, from a dispensing nozzle, the tube pulled away from the dispensing nozzle and transversely sealed, and is then cut to individual packaging units at the areas of the transverse sealing. To achieve satisfactory sterility, the immersion time needs to be 30 seconds or more when passed through a sterilising bath, which requires a substantial amount of space if the packaging machine operates at speed.

In order to maintain the sterility of the laminate during the processes of slitting and feeding into the relevant filling machinery, this all needs to be carried out under sterile conditions, i.e. the entire area between the laminate sterilisation and the finished package has to be pre-sterilised and then maintained. A sterile enclosure for such machinery and its associated equipment may, for example, be from the laminate reel to the point where the product is sealed into the packaging. This technique is well-known, but no access for operators to the space in question can be allowed without breaching the sterile area, so if, for any reason, access does need to occur, then before the machine can be brought back into operation, the interior of the enclosure must be re-sterilised, which involves significant downtime.

It is known to sterilise substantial volumes of enclosed space by using a fine plasma mist. The sterilisation technology which employs this was developed for the sterilisation of contaminated areas, such as laboratories, hospitals and clean rooms, and commercial equipment for doing so is available. Plasma mist technology uses a proprietary low concentration of hydrogen peroxide as its main active ingredient as well as other gases and passes the solution through an atmospheric cold plasma arc, which produces a highly reactive oxygen species. This species, which is commonly known as ozone, kills and inactivates bacteria, viruses and mould spores by lysis of proteins, carbohydrates and lipids leaving the hospital room free of the pathogens that are typically found in hospitals and healthcare environments.

Plasma mist technology is described in, for example, WO 2003/103726, US-A-2014/0322096 and US-A-2016/0361454.

SUMMARY OF THE INVENTION

The present invention solves the problems associated with sterilisation of packaging for fluent material and provides a device and method for forming individual tubes or sachets containing fluent material.

The present invention is directed to a packaging machine with a filling head adapted to form packaging from a strip of foil or laminate material into a closed foil or laminate tube or sachet by folding the material about a dispensing tube from which fluent material is dispensed to fill the tube or sachet and which is characterised by means for injecting a mist of plasma into the interior of the foil or laminate tube or sachet as it is formed, and extracting the mist from the area once it has passed over the interior walls of the foil or laminate tube or sachet being formed.

The present invention is also directed to a method of forming individual foil or laminate tubes or sachets containing fluent material using a packaging machine with a filling head characterised by exposing the side of the foil or laminate from which the tubes are made, and which will be in contact with the fluent material when the tune or sachet is formed, to plasma in mist or aerosol form as the tube or sachet is formed on the packaging machine.

BRIEF DESCRIPTION OF THE DRAWINGS

These and other features, aspects and advantages of the present invention will become better understood with reference to the following description, appended claims, and accompanying drawing where:

FIG. 1 is a front cross-section view of a filling head on a filling machine modified in accordance with the present invention.

DETAILED DESCRIPTION OF THE INVENTION

We have now found that plasma mist technology may be used effectively to sterilise the interior of the packaging as the packages are formed and filled.

According to a first feature of the present invention, there is provided a method of forming individual foil tubes or sachets containing fluent material which is characterised by exposing the side of the foil which will be in contact with the fluent material when the package is formed to plasma in mist or aerosol form as the tube or sachet is formed on the packaging machine.

In accordance with a second feature of the invention, there is provided a packaging machine of known construction which is adapted to form packaging from a laminate material into a closed tube or sachet by folding the material about a dispensing tube from which the fluent material is dispensed and which is characterised by means for injecting a mist of plasma into the interior of the laminate of the material tube as it is formed, and extracting the mist from the area once it has passed over the interior walls of the laminate tube being formed.

As depicted in FIG. 1, this can be achieved by surrounding the dispensing tube with a cylindrical pipe having an open end adjacent the dispensing tube and providing a tapered or stepped construction to a forming tube about which the laminate is folded, enabling the mist to flow past the laminate surface as the package is formed and thus sterilise that surface before it comes into contact with the product in question and then to reverse direction and flow into the open end of the pipe surrounding the dispensing tube. The forming tube may have apertures through which the mist may be extracted and this is preferably in the form of a jacket with an extraction orifice so that the mist can be exhausted to a suitable receptacle.

The sterile package is accordingly capable of being produced without the need for locating the entire packaging machine in a sterile environment. The sterilisation of the packaging material takes place between the construction of the package and filling the package, so dramatically reducing the extent of the equipment that has to be kept in a sterile environment. The plasma mist does not contaminate the product because on contact with it, it breaks down into water and oxygen, and in very small amounts.

The plasma mist may be generated using conventional plasma generation equipment, for example as described in the specifications noted above. When used in the method and apparatus of the present invention, the equipment includes a monitoring system which controls both the flows of the plasma mist into and out of the sterile area and also controls the makeup of the mist ensuring that the concentration of the products through the plasma gun are constant. This enables the sterilisation of the packaging material to be sterilised in controlled conditions. To maintain these at an optimum level, this monitoring is preferably constant and integrated into the packaging machine.

The invention is illustrated by way of example with reference to the accompanying drawing which shows diagrammatically a filling head on a filling machine modified in accordance with the invention.

Referring to FIG. 1:

In known fashion, a strip of laminate material 1 is fed downwardly as shown in the drawing and formed around a forming tube former 2 to form a tube. Located centrally and coaxially to forming tube former 2 is a filling tube 3. The product to be contained in the sealed packages is pumped into the upper end of tube 3 and emerges at the lower end of tube 3 in the form of a stream of fluent material 4. Downstream of the lower end of tube 3, the laminate tube is heat-sealed across, diagrammatically indicated as area 5, so as to leave below area 5 (and above the previous area 5, not shown) a sealed package. Individual packages may be made by transversely cutting across the seal areas 5, at the level indicated by A-A on the drawing.

In accordance with the invention, the filling tube 3 is surrounded by a tube 6 centred on the filling tube, to define an inner annular space between tube 3 and tube 6 and an outer annular space between tube 6 and the tube formed from the strip of laminate material 1.

The upper end of tube 6 is an inlet pipe 10 via which a plasma mist may be injected into the outer annular space between former 2 and tube 6 and then between the laminate material and tube 6. The mist flows down the outer annular space and then, because tube 6 terminates just above the outlet orifice of tube 3, it flows back up the outer annular space, thus passing over the entire interior wall area of the laminate which has been formed into a tube. At the top of tube 6 is an exhaust port 11 from which the mist is extracted. The outer surface of tube 6 has a helical ridge 12 (this may not be required on all packaging machines) on it which causes the mist to spiral around the interior of the laminate tube so as to ensure complete sterilisation of the interior wall of the laminate tube. This ridge may not be required for larger packages. The plasma inlet (10) and exhaust port (11) could be reversed so that the plasma inlet is (11) and extraction is through (10).

When running continuously, the speed at which the tube is lowered in the direction of arrow 15 on the drawing, and the rate at which the fluent material 4 is pumped from the end of tube 3, are adjusted so that the individual sachets are filled to the desired degree. The degree of sterilisation achieved will depend on the passage time over which the mist passes down over the interior wall of the recently formed laminate tube and in contact with its interior surface. This distance is denoted B in FIG. 1.

By way of example, we have found that if the machine is set to operate producing one package per second, each package being 120 mm long, then if the distance B is less than 500 mm, then the interior of the tube will be exposed to the mist for approximately five seconds. This provides satisfactory sterilisation.

The invention claimed is:

1. A filling head on a packaging machine for filling tubes or sachets with fluent material comprising:
    a dispensing tube having an open upper end and an open lower end through which fluent material is dispensed;
    a forming tube surrounding the dispensing tube, the forming tube positioned near an upper portion of the dispensing tube and extending to an open end positioned such that the dispensing tube extends beyond the open end of the forming tube;
    the forming tube having an outer wall being a former and an inner wall creating a tube about the dispensing tube, the forming tube defining a first annular space between the outer wall and an outer surface of the inner wall and a second annular space between an inner surface of the inner wall and an outer wall of the dispensing tube;
    an inlet pipe in fluid communication with the first or second annular space and an exhaust port in fluid communication with the second or first annular space respectively, the inlet pipe and the exhaust port located at an upper end of the forming tube;
    a strip of laminate material, the strip of laminate material fed from the upper end of the forming tube past the lower end of the dispensing tube to form a tube or sachet such that the laminate material surrounds the forming tube and the portion of the dispensing tube extending beyond the forming tube and creates a closed space containing at least a portion of the forming tube and the portion of the dispensing tube extending beyond the forming tube; and
    a plasma mist containing a highly reactive oxygen species, the plasma mist injected into the forming tube as the laminate material passes over the forming tube and the dispensing tube such that the plasma mist flows through the first annular space and the second annular space, thereby exposing an inner surface of the laminate material, the forming tube, and the outer surface of the dispensing tube to plasma mist.

2. The filling head on a packaging machine of claim 1, wherein the inner wall of the forming tube extends beyond the outer wall of the forming tube.

3. The filling head on a packaging machine of claim 2, wherein the outer surface of the inner wall includes a helical ridge.

4. A method of filling a tube or sachet on a filling machine comprising:
   a. providing a filling head comprising:
      i. a dispensing tube having an open upper end and an open lower end through which fluent material is dispensed;
      ii. a forming tube surrounding the dispensing tube, the forming tube positioned near an upper portion of the dispensing tube and extending to an open end positioned such that the dispensing tube extends beyond the open end of the forming tube;
      iii. the forming tube having an outer wall being a former and an inner wall creating a tube about the dispensing tube, the forming tube defining a first annular space between the outer wall and an outer surface of the inner wall and a second annular space between an inner surface of the inner wall and an outer wall of the dispensing tube; and
      iv. an inlet pipe in fluid communication with the first or second annular space and an exhaust port in fluid communication with the second or first annular space respectively, the inlet pipe and the exhaust port located at an upper end of the forming tube;
   b. providing a strip of laminate material, the strip of laminate material fed from the upper end of the forming tube past the lower end of the dispensing tube to form a tube or sachet such that the laminate material surrounds the forming tube and the portion of the dispensing tube extending beyond the forming tube and creates a closed space containing at least a portion of the forming tube and the portion of the dispensing tube extending beyond the forming tube;
   c. injecting a plasma mist containing a highly reactive oxygen species, the plasma mist injected into the forming tube as the laminate material passes over the forming tube and the dispensing tube such that the plasma mist flows through the first annular space and the second annular space, thereby exposing an inner surface of the laminate material, the forming tube, and the outer surface of the dispensing tube to plasma mist; and
   d. pumping fluent material through the dispensing tube such that the fluent material fills the tube or sachet.

\* \* \* \* \*